United States Patent
Miao et al.

(10) Patent No.: US 10,684,219 B2
(45) Date of Patent: Jun. 16, 2020

(54) METHOD FOR DETERMINING HYDROCARBON CONCENTRATION IN DRILLED SOLIDS USING NEAR INFRARED SPECTROSCOPY

(71) Applicant: Chevron U.S.A. Inc., San Ramon, CA (US)

(72) Inventors: Toni Zhang Miao, Orinda, CA (US); John Bryan Trenery, Jr., Sugar Land, TX (US); Deyuan Kong, San Ramon, CA (US); Roopa Kamath, Rumbai (ID); Robert Neil Trotter, Conroe, TX (US); Cory James McDaniel, Sausalito, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 42 days.

(21) Appl. No.: 16/175,156

(22) Filed: Oct. 30, 2018

(65) Prior Publication Data
US 2020/0132597 A1 Apr. 30, 2020

(51) Int. Cl.
*G01N 33/24* (2006.01)
*G01N 21/359* (2014.01)

(52) U.S. Cl.
CPC ......... *G01N 21/359* (2013.01); *G01N 33/241* (2013.01)

(58) Field of Classification Search
CPC .............................. G01N 21/359; G01N 33/241
See application file for complete search history.

(56) References Cited

U.S. PATENT DOCUMENTS

| 5,161,409 A | 11/1992 | Hughes et al. |
| 5,306,909 A * | 4/1994 | Jones ................. G01N 21/3577 250/255 |
| 8,914,312 B2 | 12/2014 | McLaughlin et al. |

(Continued)

OTHER PUBLICATIONS

Raphael, Linker; "Application of FTIR Spectroscopy to Agriculture Soils Analysis"; (2011), Fourier Transforms—New Analytical Approaches and FTIR Strategies, Prof. Goran Nikolic (Ed.), ISBN: 978-953-307-232-6, InTech, Available from http://www.intechopen.com/books/fourier-transforms-new-analytical-approaches-and-ftir-strategies/application-of-ftir-spectroscopy-to-agricultural-soils-analysis.

*Primary Examiner* — Violeta A Prieto
(74) *Attorney, Agent, or Firm* — Karen DiDomenicis; Parul P. Anderson (57) ABSTRACT

Hydrocarbons concentrations are determined in drilling cuttings samples by generating a model for predicting hydrocarbons concentrations. Methods include dividing multiple samples removed from drilling fluid into two one set analyzed using a retort, and another set analyzed using a handheld NIR spectrometer to obtain NIR diffuse reflectance data. PLS analysis is used to correlate the retort data with the diffuse reflectance data to generate a calibration model. The model is validated with samples having unknown hydrocarbons concentration. The model is used to predict the hydrocarbons concentration for samples removed from drilling fluid taken from the rig site using the spectrometer to obtain diffuse reflectance data. During measurements, each sample contains 0.1 to 10 wt % moisture and each sample is in a clear container pressed against the spectrometer window such that the IR source from the handheld device can pass to the drilled solids sample within the clear container without opening the clear container.

13 Claims, 4 Drawing Sheets

(56) References Cited

U.S. PATENT DOCUMENTS

| | | | |
|---|---|---|---|
| 9,134,227 B2 * | 9/2015 | Janik | G01N 21/274 |
| 9,606,088 B2 | 3/2017 | Spartz et al. | |
| 9,841,321 B2 | 12/2017 | Pastore et al. | |
| 10,041,926 B2 | 8/2018 | Miao et al. | |
| 2012/0226653 A1 | 9/2012 | McLaughlin et al. | |
| 2012/0318982 A1 * | 12/2012 | Janik | G01N 21/274 |
| | | | 250/339.11 |
| 2014/0197316 A1 * | 7/2014 | Kadali | G01N 21/274 |
| | | | 250/339.11 |
| 2017/0160136 A1 | 6/2017 | Spartz et al. | |
| 2017/0299431 A1 | 10/2017 | Pastore et al. | |
| 2018/0017540 A1 * | 1/2018 | Miao | G01N 21/3563 |

* cited by examiner

METHOD FOR DETERMINING HYDROCARBON CONCENTRATION IN DRILLED SOLIDS USING NEAR INFRARED SPECTROSCOPY

FIELD

The present disclosure relates generally to methods to determine the concentration of hydrocarbon in drilling cuttings using a handheld near infrared (NIR) spectroscopy device with diffuse reflectance data and partial least squares (PLS) analysis.

BACKGROUND

Drilling fluids, also referred to as drilling muds, are commonly used to drill oil and gas wells. Drilling fluids are mixtures of oil, brine, emulsifiers and solids to create the properties needed to provide borehole stability and remove drilled solids, also referred to as cuttings, from the well. These fluids provide excellent drilling performance, but they are expensive, and disposal is regulated. While drilling oil and gas wells, solids control equipment including shale shakers, mud cleaners, centrifuges, etc., is used to remove drilled solids from the drilling mud. As drilled solids are removed, some of the drilling fluid is removed with them. When the well is completed, the removed solids must be disposed of. Most government disposal regulations specify a maximum amount of oil on the drilled solids that must be met before disposal can occur.

The percentage of hydrocarbons on cuttings, also referred to as oil-on-cuttings, can be used to determine how much drilling fluid is lost with the drilled cuttings as they are removed. Currently, many service providers do not even test for this value. Instead, they simply make an assumption based upon the total volume of fluid they have accumulated during the day.

The oil-on-cuttings can also be used to determine compliance with local environmental regulations before the disposal of the solids. Currently, service providers use a retort to determine this value. Retorts can be used to measure the volume percentages of oil, water and solids in a drilled solids sample. A retort is a well-known device that heats a sample to separate fluids from solids by evaporation, resulting in percentage solid, percentage water and percentage oil. This test takes hours to set-up and complete, has a high degree of inaccuracy, and therefore is only used when necessary. Typically, only two or three retorts are run during a 24-hour period, despite waste being discharged during the entire 24-hour period. Monitoring oil-on-cuttings more frequently and using it to optimize drilling fluid dilution volumes and solids control equipment is desired to reduce overall drilling costs. Furthermore, more accurate and more frequent measurement of the oil-on-cuttings value is desired to ensure environmental regulatory compliance.

Another known way to measure oil-on-cuttings is using a device known as the InfraCal® TOG/Hydrocarbon Analyzer (available from Spectro Scientific, previously Wilks Enterprise, Inc.) for measuring total oil and grease (TOG) and total petroleum hydrocarbon (TPH) levels. This device requires a solvent extraction and analysis by infrared spectroscopy with attenuated total reflection (ATR) after removal of the solvent.

There still exists a need for a quicker and more accurate method for estimating total petroleum hydrocarbons concentration in drilling cuttings without using solvent.

SUMMARY

In general, in one aspect, the disclosure relates to methods to determine the concentration of hydrocarbon in drilling cuttings using a handheld near infrared (NIR) spectroscopy device with diffuse reflectance data and partial least squares (PLS) analysis. The method includes collecting, homogenizing and dividing a plurality of drilled solids samples taken from a drill rig site into a first set of drilled solids samples and a second set of drilled solids samples. The first set of samples is analyzed using a retort in a laboratory to obtain hydrocarbon concentration data. The second set of samples is analyzed using the handheld NIR spectroscopy device with a diffuse reflectance window to obtain NIR diffuse reflectance data. Partial least squares regression analysis is used to correlate the hydrocarbon concentration data with the NIR diffuse reflectance data to generate a calibration model which is the site specific predictive model, also referred to herein as the site-specific PLS model, for hydrocarbon concentration for the rig site. To validate the model, a plurality of validation drilled solids samples having unknown hydrocarbon concentration is analyzed using the handheld NIR spectroscopy device to obtain NIR diffuse reflectance data for the validation drilled solids samples. During all NIR diffuse reflectance measurements, each of the drilled solids samples has a moisture content of from 0.1 wt % to 10 wt % with no solvent added. Each sample is contained in a clear container and aligned with the diffuse reflectance window such that the IR source from the handheld device can pass to the drilled solids sample within the clear container without opening the clear container. The NIR diffuse reflectance data for the validation drilled solids samples are used to predict the hydrocarbon concentration of the validation drilled solids samples using the site specific predictive model. The hydrocarbon concentration of the validation drilled solids samples is measured using a retort. The predicted hydrocarbon concentration of the validation drilled solids samples is compared with the hydrocarbon concentration of the validation drilled solids samples as measured using the retort.

In another aspect, a drilled solids sample as a validation sample taken from the field site having an unknown hydrocarbon concentration is analyzed using the handheld NIR spectroscopy device to obtain NIR diffuse reflectance data for the drilled solids sample. The site specific predictive model generated using the method described above is then used to predict the hydrocarbon concentration of the drilled solids sample.

BRIEF DESCRIPTION OF THE DRAWINGS

These and other objects, features and advantages of the present invention will become better understood with reference to the following description, appended claims and accompanying drawings. The drawings are not considered limiting of the scope of the appended claims. Reference numerals designate like or corresponding, but not necessarily identical, elements. The drawings illustrate only example embodiments. The elements and features shown in the drawings are not necessarily to scale, emphasis instead being placed upon clearly illustrating the principles of the example embodiments. Additionally, certain dimensions or positionings may be exaggerated to help visually convey such principles.

DETAILED DESCRIPTION

Described below is a method for determining a concentration of hydrocarbons in drilled solids removed from a well on location at a drilling rig site. The rig site can be located onshore or offshore. In one embodiment, provided is a method using near infrared spectroscopy as a rapid screening tool to determine the concentration of hydrocarbons in drilling cuttings, also referred to as oil-on-cuttings. Drilling cuttings are also referred to as drilled solids herein. The drilled solids are returned with drilling fluid having been used in drilling a well. The drilled solids are removed from the drilling fluid so that the drilling fluid can be reused. The drilling fluid can be one of any number of suitable fluids, including but not limited to oil-based ($CaCl_2$ brine), oil-based (NaCl brine), fresh/brackish seawater, lime treated, gypsum treated, KCl treated, saturated NaCl or mixed salt. The removed drilled solids must meet a maximum level of percentage oil content before being discharged. For example, in some regions, local regulations require no more than 15% by weight of the cuttings as oil. If the oil contamination exceeds this level, they may be segregated and transported for disposal in special landfills, for example.

Figure 1:
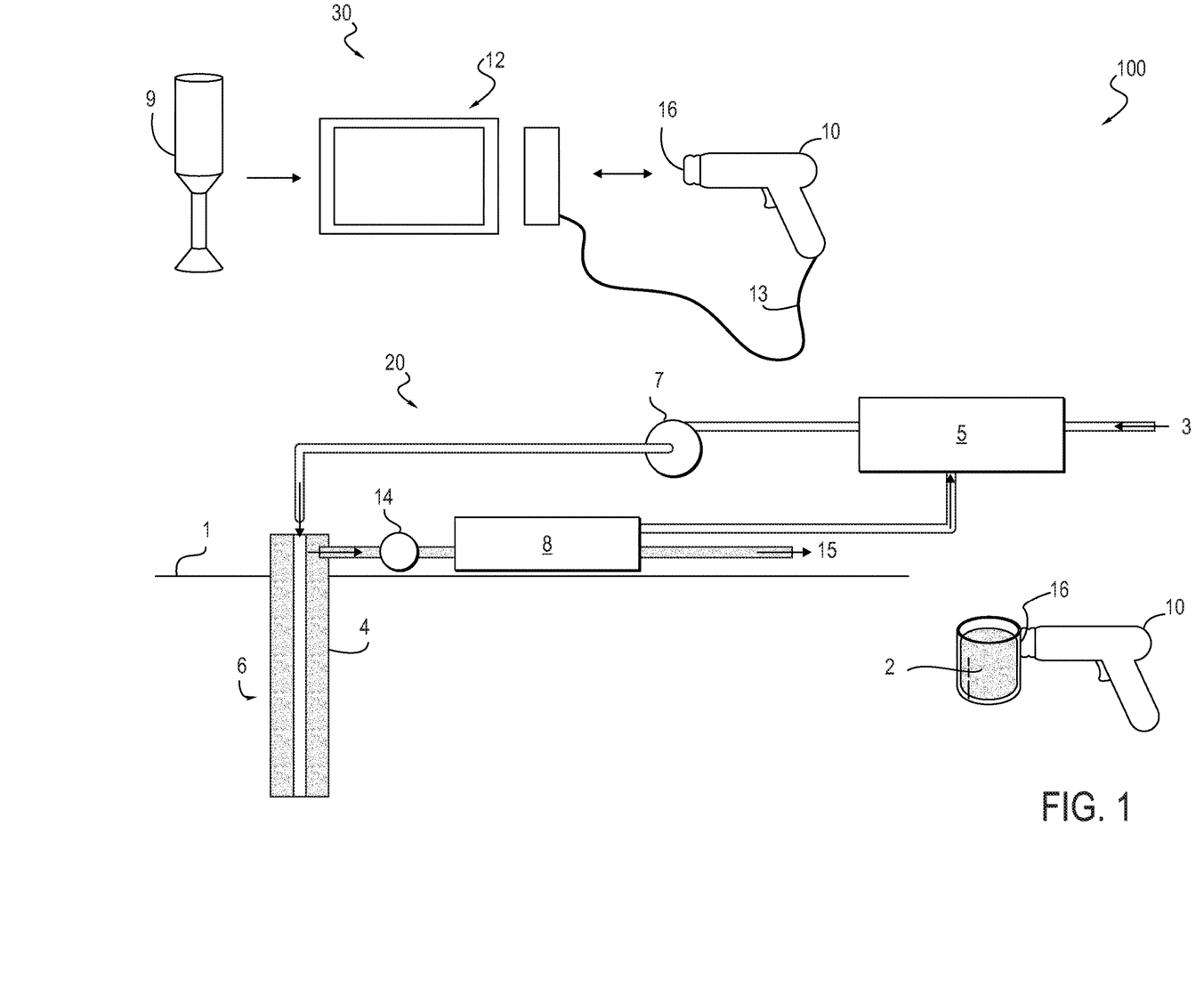
FIG. 1 shows a simplified schematic diagram of a rig site in which example embodiments can be applied.

Referring to FIG. 1, shown is a field system 100 in which methods of the disclosure are carried out. At a rig site 20, a well 6 has been drilled. Fresh drilling fluid 3 is used to drill the well 6. Drilling fluid 3 can be stored in a drilling fluid tank 5 and pumped downhole using pump 7. In the annulus of the well 6, used drilling fluid containing drilled solids 4 is returned to the surface 1. The used drilling fluid 4 is sent to solids control equipment 8. The solids control equipment 8 can include any suitable equipment for segregating and removing drilled solids such as, but not limited to, shale shakers, centrifuges, mud cleaners, and the like. Drilled solids 15 are removed from the solids control equipment 8 for disposal also referred to herein as discharge.

The drilled solids 15 can include hydrocarbons such as but not limited to lubricant oil, base oil, grease, diesel and combinations thereof.

In one embodiment, a site specific PLS model used to translate the near infrared diffuse reflectance data into hydrocarbon concentration on drilled solids is provided. The site specific predictive model is used for determining the concentration of hydrocarbons in drilled solids 15 removed from drilling fluid 4 used in drilling a well 6. The method includes collecting, homogenizing and dividing a plurality of drilled solids samples taken from the drilling rig site 20 into a first set of drilled solids samples and a second set of drilled solids samples such that the first and second sets of drilled solids samples are substantially equivalent for purposes of predictive model calibration.

The first set of drilled solids samples is analyzed using a retort 9 in a laboratory or other off-site location 30 to obtain hydrocarbon concentration data. The retort 9 dries each sample to constant weight and measures percentage solids by volume and by weight, allowing an average solids density to be calculated. The average solids density is used to calculate a percentage "high gravity solids" (assuming a high gravity solids density, $\rho_{hgs}$=4.3 kg/l) and a percentage of "low gravity solids" (assuming a low gravity solids density $\rho_{lgs}$=2.5 kg/l).

The second set of samples of drilled solids are placed in clear containers 2 at the rig site 20. Suitable containers 2 include clear plastic bags, clear plastic bottles, clear glass bottles and the like. The drilled solids samples are placed in the containers without drying the samples or adding solvent to the samples, placing each of the second set of drilled solids samples into a clear container such that at least a portion of the clear container makes visible the drilled solids from the exterior of the clear container.

Figure 2:
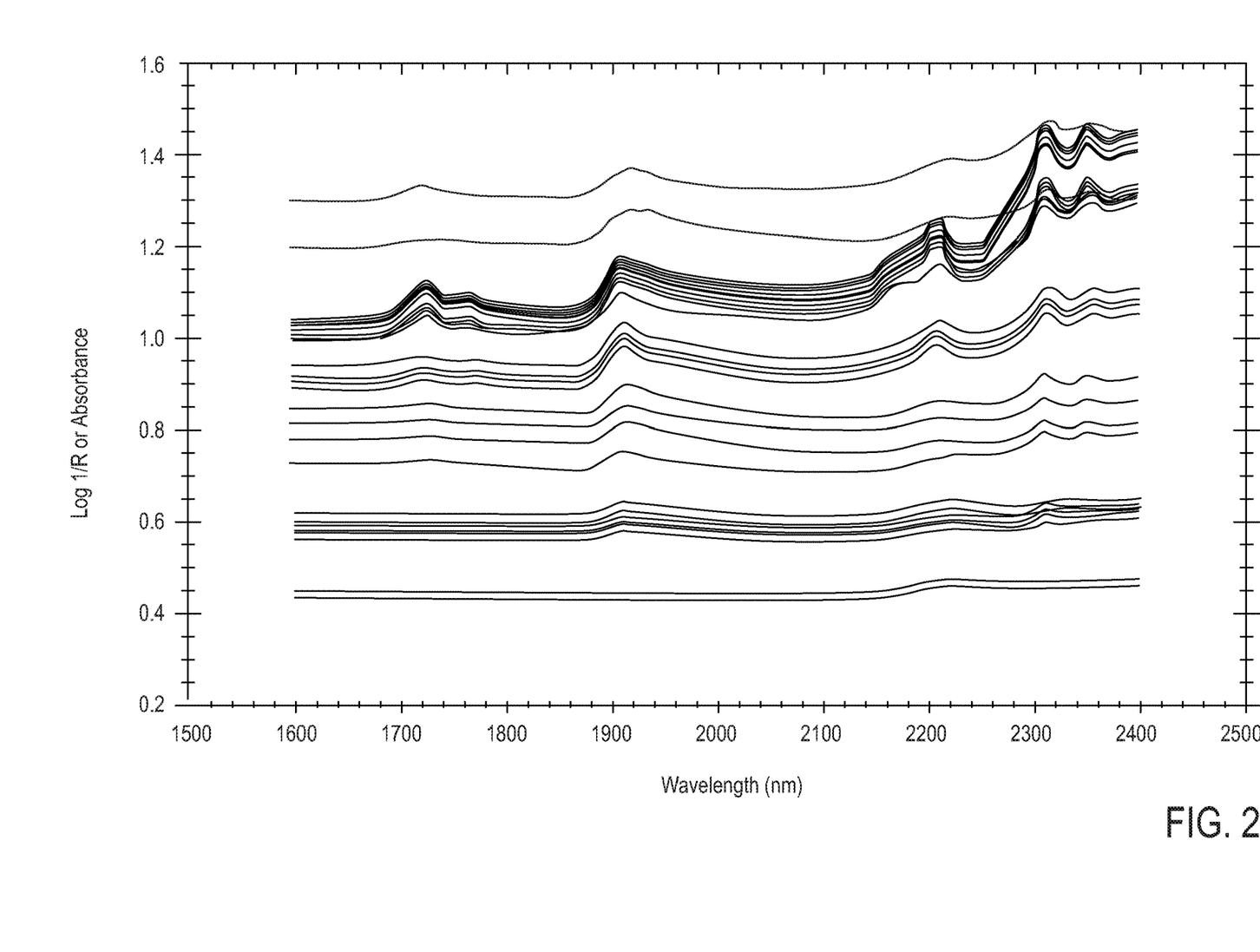
FIG. 2 is an NIR overlay spectrum for use in example embodiments.

The second set of drilled solids samples is analyzed using the handheld NIR spectroscopy device 10 having a spectrometer therein, also referred to herein as the handheld device and the handheld NIR device, 10 with a diffuse reflectance window to obtain NIR diffuse reflectance data. The handheld NIR device 10 is used to measure the near infrared spectrum of a sample of the drilled solids removed from drilling fluid 4, where the sample is within the clear container 2. FIG. 2 illustrates a NIR spectrum overlay obtained using the handheld MR device 10. Near infrared, also referred to as NIR, spectroscopy is based on the near infrared diffuse reflectance data in the combination and first overtone spectral bands for CH, $CH_2$ and $CH_3$. In one embodiment, NIR wave numbers suitable for use in the invention can range from 4300 $cm^{-1}$ to 8000 $cm^{-1}$.

A Thermo MicroPHAZIR® NIR spectroscopy device 10 (available from Thermo Fischer Scientific Inc.) with built-in Micro-Electrical-Mechanical (MEMS) technology can be used as the handheld device 10. The handheld device 10 is designed to be portable and handheld for rapid on-site or field measurement. At an offsite location 30, the handheld device 10 can connect via a USB cable 13 to a personal computer (PC) 12 for data and calibration model synchronization. The handheld device 10 has a diffuse reflectance window 16 that allows the NIR spectrum to be collected from a sample when placed in contact or alignment with the container 2 containing the sample. The handheld near infrared spectroscopy device 10 can obtain near infrared diffuse reflectance data within about 3 seconds.

During the NIR diffuse reflectance measurements, each clear container 2 containing a sample is contacted and aligned with the diffuse reflectance window 16 such that the IR source from the handheld device 10 can pass to the drilled solids sample within the clear container 2 without opening the clear container. A plurality of replicate spectra of near infrared diffuse reflectance data is thus obtained for each of the separate drilled solids samples. In some embodiments, more than two replicate spectra are obtained, even more than three, even more than four and even more than five, for each drilled solids sample.

The methods disclosed can advantageously be applied to drilled solids samples having from 0.1 to 10 wt % water, even from 1 to 5 wt % water, without the need for solvent extraction from the samples or for drying of the samples.

Partial least squares (PLS) regression analysis is used to correlate the hydrocarbon concentration data from the retort 9 with the NIR diffuse reflectance data to generate a calibration model within the PC 12 which is the site specific PLS model for hydrocarbon concentration for the rig site 20. In some embodiments, the peak area of the NIR diffuse reflectance data in the combination and first overtone spectral bands for CH, $CH_2$ and $CH_3$ is integrated to provide an indication of hydrocarbon concentration based on the PLS regression analysis to correlate the hydrocarbon concentration data from the retort with the NIR diffuse reflectance data. In some embodiments, the PLS regression analysis uses three factor correlation to correlate the hydrocarbon concentration data obtained using the retort with the near infrared diffuse reflectance data to generate the site specific PLS model.

FIG. 2 is an example of an overlay spectra of calibration samples in the wavenumber 4300-8000 cm$^{-1}$. In some embodiments for the development of PLS calibration model, the peak area of the NIR diffuse reflectance data for CH, $CH_2$ and $CH_3$ in the combination and first overtone spectral bands can be used to provide hydrocarbon concentration ranges based on the PLS regression analysis.

To validate the PLS model generated, a plurality of validation drilled solids samples having unknown hydrocarbon concentration is analyzed using the handheld NIR device 10 to obtain NIR diffuse reflectance measurements. During such NIR diffuse reflectance measurements, each of the drilled solids samples has a moisture content of from 0.1 to 10 wt %, even from 1 to 5 wt %. Each clear container 2 containing a sample is pressed against and aligned with the diffuse reflectance window 16 such that the IR source from the handheld device 10 can pass to the drilled solids sample within the clear container 2 without opening the clear container. The NIR diffuse reflectance data for the validation drilled solids samples are used to predict the hydrocarbon concentration of the validation drilled solids samples using the rig site specific PLS model. The hydrocarbon concentration of the validation drilled solids samples is measured using the retort 9. Calculated NIR diffuse reflectance data and measured hydrocarbon concentration data from the retort 9 are subjected to regression analysis and the coefficient of determination $R^2$ is determined to indicate the ability of the calibration model to predict and quantify hydrocarbon concentration in drilled solids samples taken from the same rig site 20. The $R^2$ value indicates whether the site specific PLS model can provide acceptable prediction of hydrocarbon concentration in drilled solids at rig site 20.

Once the model is validated, the model can be used to determine hydrocarbon concentrations of drilled solids samples having unknown hydrocarbon concentrations where the samples are taken from the same rig site 20 from whence the drilled solids samples came to develop the model. For example, a drilled solids sample having an unknown hydrocarbon concentration can be taken at the rig site 20 and analyzed using the handheld NIR device 10 to obtain NIR diffuse reflectance data. Using the site specific PLS model loaded into the handheld NIR device 10, the unknown hydrocarbon concentration of the drilled solids sample is determined by the model and is quickly displayed to a user in the display of the handheld device 10 at the rig site 20. Again, during all NIR diffuse reflectance measurements, each of the drilled solids samples has a moisture content of from 0.1 to 10 wt %, even from 1 to 5 wt %, and each clear container 2 is contacted and aligned with the diffuse reflectance window 16 such that the IR source from the handheld device 10 can pass to the drilled solids sample within the clear container 2 without opening the clear container. The handheld NIR device 10 can be used on location at the rig site 20 to measure oil on cuttings prior to discharging the cuttings to determine whether the cuttings 15 require further cleaning before disposal or alternative disposal. In one embodiment, the handheld NIR device 10 can be used on location at a drilling rig site 20 to measure oil on cuttings being discharged from solids control equipment 8.

In another embodiment, once the model is validated, the model can be used to determine hydrocarbon concentrations of drilled solids having unknown hydrocarbon concentration where the drilled solids are continuously monitored by a NIR sensor 14 in a section of pipe at the rig site 20. In this embodiment, the NIR sensor 14 collects diffuse reflectance data that is then sent to a processor, e.g., in PC 12. The processor on a continuous basis can then use the site specific PLS model to determine the hydrocarbon concentration of drilled solids passing through the section of pipe that includes the sensor 14. The section of pipe can be located upstream or downstream of the solids control equipment 8 at the rig site 20.

In one embodiment, the concentration level of hydrocarbons on drilled solids can be controlled by using the model to determine whether the concentration level of hydrocarbons on drilled solids has exceeded a desired maximum level. The model can determine the concentration level of hydrocarbons on drilled solids either using the handheld device 10 at the rig site 20 or using a NIR sensor 14 in a section of pipe at the rig site 20. When it is determined that the concentration level of hydrocarbons on the drilled solids is excessive, a mitigation step can be implemented. For instance, the pump 7 can be used to increase the rate of fresh drilling fluid 3 being pumped into the well 6.

EXAMPLES

A calibration model was prepared using 20 samples divided into two sets of samples of drilled solids prepared having from 1 to 28 wt % hydrocarbons on the drilled solids samples.

A first set of samples was measured with a retort.

The drilled solids in the second set of samples were placed into a glass vial with a flat surfaced bottom into a glass vial with a flat surfaced bottom and pressed down with little pressure to consolidate the sample. A portable handled NIR Thermo MicroPHAZIR® analyzer (available from Thermo Fischer Scientific Inc.) with built-in micro-electrical-Mechanical (MEMS) technology was used to collect NIR diffuse reflectance data. The absorption in the combination and first overtone spectral bands for CH, $CH_2$ and $CH_3$ at 4300-8000 cm$^{-1}$ were collected and each sample was analyzed four to five times.

The replicated spectra were recorded from each of the 20 calibration samples and obtained for each of the separate drilled solids samples.

Five samples were unknown samples used to validate of the calibration model.

Pretreatment of the NIR raw data, was applied validated Partial least squares (PLS) regression analysis to correlate the hydrocarbon concentration from the retort 9 with first derivative of the NIR diffuse reflectance data to generate a calibration model which is the site specific PLS model for hydrocarbon concentration for the rig site 30. In FIG. 2, the overlay spectra of the 20 calibration samples are shown in the wavenumber 4300-8000 cm$^{-1}$. In some embodiments for the development of PLS calibration model, the peak area of the NIR diffuse reflectance data for CH, $CH_2$ and $CH_3$ in the combination and first overtone spectral bands was used to provide hydrocarbon concentration ranges based on the PLS regression analysis. Based on 3 factors very good calibration have been obtained the hydrocarbon concentration from the retort data.

See Table 1 for the results of the two sets of samples for generating the calibration model, and the validation samples for validating the calibration model.

TABLE 1

| Scan ID | Sample location ID | Name | Oil wt % Actual (retort) | Oil Wt % Calculated (calibration model) | Deviation | Square of Deviation | Deviation from Mean (0-41.0% set) | Square of Deviation |
|---|---|---|---|---|---|---|---|---|
| 130 | u9 | Calibration | 1.12 | 1.326298 | 0.206 | 0.043 | −9.125 | 83.266 |
| 131 | u9 | Calibration | 1.12 | 1.489573 | 0.370 | 0.137 | −8.962 | 80.313 |
| 132 | u9 | Calibration | 1.12 | 1.412711 | 0.293 | 0.086 | −9.039 | 81.697 |
| 133 | u9 | Calibration | 1.12 | 1.393724 | 0.274 | 0.075 | −9.058 | 82.040 |
| 134 | u9 | Calibration | 1.12 | 1.194157 | 0.074 | 0.005 | −9.257 | 85.695 |
| 26 | dm9 | Validation | 1.88 | 1.82042 | −0.060 | 0.004 | −8.631 | 74.493 |
| 27 | dm9 | Validation | 1.88 | 1.727634 | −0.152 | 0.023 | −8.724 | 76.103 |
| 28 | du9 | Validation | 1.88 | 1.932:511 | 0.053 | 0.003 | −8.519 | 72.570 |
| 29 | dm9 | Validation | 1.88 | 1.473258 | −0.407 | 0.165 | −8.978 | 80.606 |
| 30 | din9 | Validation | 1.88 | 1.462377 | −0.418 | 0.174 | −8.989 | 80.801 |
| 102 | u5 | Calibration | 3.26 | 2.15355 | −1.106 | 1.224 | −8.298 | 68.853 |
| 103 | u5 | Calibration | 3.26 | 1.929021 | −1.331 | 1.772 | −8.522 | 72.630 |
| 104 | u5 | Calibration | 3.26 | 1.967836 | −1.292 | 1.670 | −8.483 | 71.970 |
| 105 | u5 | Calibration | 3.26 | 1.84133 | −1.419 | 2.013 | −8.610 | 74.132 |
| 106 | u5 | Calibration | 3.26 | 2.103893 | −1.156 | 1.337 | −8.347 | 69.680 |
| 12 | dm10 | Calibration | 3.89 | 2.615416 | −1.275 | 1.625 | −7.836 | 61.402 |
| 13 | dm10 | Calibration | 3.89 | 2.65466 | −1.235 | 1.526 | −7.797 | 60.788 |
| 14 | dm10 | Calibration | 3.89 | 2.270131 | −1.620 | 2.624 | −8.181 | 66.932 |
| 15 | dm10 | Calibration | 3.89 | 2.737585 | −1.152 | 1.328 | −7.714 | 59.502 |
| 16 | dm10 | Calibration | 3.89 | 2.685145 | −1.205 | 1.452 | −7.766 | 60.314 |
| 54 | dtn419 | Calibration | 4.19 | 5.45132 | 1.261 | 1.591 | −5.000 | 25.000 |
| 55 | dm419 | Calibration | 4.19 | 5.369429 | 1.179 | 1.391 | −5.082 | 25.826 |
| 56 | dm419 | Calibration | 4.19 | 5.251362 | 1.061 | 1.126 | −5.200 | 27.040 |
| 57 | dm419 | Calibration | 4.19 | 5.293923 | 1.104 | 1.219 | −5.157 | 26.599 |
| 58 | dm419 | Calibration | 4.19 | 5.012991 | 0.823 | 0.677 | −5.438 | 29.575 |
| 19 | dm2 | Validation | 4.24 | 4.114472 | −0.126 | 0.016 | −6.337 | 40.156 |
| 20 | dm2 | Validation | 4.24 | 4.163422 | −0.077 | 0.006 | −6.288 | 39.538 |
| 21 | dm2 | Validation | 4.24 | 4.151245 | −0.089 | 0.008 | −6.300 | 39.691 |
| 22 | dm2 | Validation | 4.24 | 4.120725 | −0.119 | 0.014 | −6.331 | 40.077 |
| 23 | dm2 | Validation | 4.24 | 4.239952 | 0.000 | 0.000 | −6.211 | 38.581 |
| 40 | dm1 | Calibration | 5.45 | 6.15263 | 0.703 | 0.494 | −4.299 | 18.479 |
| 41 | dm1 | Calibration | 5.45 | 6.134255 | 0.684 | 0.468 | −4.317 | 18.637 |
| 42 | dm1 | Calibration | 5.45 | 6.202733 | 0.753 | 0.567 | −4.249 | 18.051 |
| 43 | dm1 | Calibration | 5.45 | 6.095068 | 0.645 | 0.416 | −4.356 | 18.977 |
| 44 | dm1 | Calibration | 5.45 | 6.06381 | 0.614 | 0.377 | −4.388 | 19.250 |
| 95 | u6 | Calibration | 5.59 | 5.041809 | −0.548 | 0.301 | −5.410 | 29.263 |
| 96 | u6 | Calibration | 5.59 | 5.095314 | −0.495 | 0.245 | −5.356 | 28.687 |
| 97 | u6 | Calibration | 5.59 | 5.078938 | −0.511 | 0.261 | −5.372 | 28.863 |
| 98 | u6 | Calibration | 5.59 | 5.16576 | −0.424 | 0.180 | −5.286 | 27.937 |
| 99 | u6 | Calibration | 5.59 | 4.755128 | −0.835 | 0.697 | −5.696 | 32.447 |
| 61 | dm563 | Validation | 5.63 | 7.998263 | 2.368 | 5.609 | −2.453 | 6.018 |
| 62 | dm563 | Validation | 5.63 | 7.290787 | 1.661 | 2.758 | −3.161 | 9.989 |
| 63 | dm563 | Validation | 5.63 | 8.284196 | 2.654 | 7.045 | −2.167 | 4.696 |
| 64 | dm563 | Validation | 5.63 | 7.632663 | 2.003 | 4.011 | −2.819 | 7.945 |
| 65 | dm563 | Validation | 5.63 | 8.218633 | 2.589 | 6.701 | −2.233 | 4.985 |
| 33 | dm8 | Calibration | 6.47 | 7.03575 | 0.566 | 0.320 | −3.416 | 11.666 |
| 34 | dm8 | Calibration | 6.47 | 6.412144 | −0.058 | 0.003 | −4.039 | 16.315 |
| 35 | dm8 | Calibration | 6.47 | 6.525942 | 0.056 | 0.003 | −3.925 | 15.409 |
| 36 | dm8 | Calibration | 6.47 | 6.369586 | −0.100 | 0.010 | −4.082 | 16.661 |
| 37 | dm8 | Calibration | 6.47 | 6.19263 | −0.277 | 0.077 | −4.259 | 18.137 |
| 47 | dm7 | Calibration | 7.56 | 7.68509 | 0.125 | 0.016 | −2.766 | 7.652 |
| 48 | dm7 | Calibration | 7.56 | 7.813287 | 0.253 | 0.064 | −2.638 | 6.959 |
| 49 | dm7 | Calibration | 7.56 | 7.892562 | 0.333 | 0.111 | −2.559 | 6.547 |
| 50 | dm7 | Calibration | 7.56 | 8.090226 | 0.530 | 0.281 | −2.361 | 5.575 |
| 51 | dm7 | Calibration | 7.56 | 8.03779 | 0.478 | 0.228 | −2.414 | 5.825 |
| 81 | u8 | Calibration | 8.1 | 8.311918 | 0.212 | 0.045 | −2.139 | 4.577 |
| 82 | u8 | Calibration | 8.1 | 7.890407 | −0.210 | 0.044 | −2.561 | 6.558 |
| 83 | u8 | Calibration | 8.1 | 7.95211 | −0.148 | 0.022 | −2.499 | 6.246 |
| 84 | u8 | Calibration | 8.1 | 8.464067 | 0.364 | 0.133 | −1.987 | 3.949 |
| 85 | u8 | Calibration | 8.1 | 8.321733 | 0.222 | 0.049 | −2.130 | 4.535 |
| 68 | dm3 | Calibration | 10.39 | 10.32181 | −0.068 | 0.005 | −0.130 | 0.017 |
| 69 | dm3 | Calibration | 10.39 | 10.5275 | 0.137 | 0.019 | 0.076 | 0.006 |
| 70 | dm3 | Calibration | 10.39 | 10.48198 | 0.092 | 0.008 | 0.031 | 0.001 |
| 71 | dm3 | Calibration | 10.39 | 9.548328 | −0.842 | 0.708 | −0.903 | 0.815 |
| 72 | dm3 | Calibration | 10.39 | 10.27972 | −0.110 | 0.012 | −0.172 | 0.029 |
| 74 | u7 | Calibration | 12.06. | 10.70778 | −1.352 | 1.828 | 0.256 | 0.066 |
| 75 | u7 | Calibration | 12.06 | 11.93433 | −0.126 | 0.016 | 1.483 | 2.199 |
| 76 | u7 | Calibration | 12.06 | 11.07131 | −0.989 | 0.978 | 0.620 | 0.384 |
| 77 | u7 | Calibration | 12.06 | 9.523031 | −2.537 | 6.436 | −0.928 | 0.862 |
| 78 | u7 | Calibration | 12.06 | 9.431028 | −2.629 | 6.911 | −1.020 | 1.041 |
| 38 | m5 | Calibration | 16.9 | 16.90203 | 0.002 | 0.000 | 6.451 | 41.612 |
| 39 | m5 | Calibration | 16.9 | 17.27301 | 0.373 | 0.139 | 6.822 | 46.535 |
| 40 | m5 | Calibration | 16.9 | 17.7145 | 0.815 | 0.663 | 7.263 | 52.754 |
| 41 | m5 | Calibration | 16.9 | 17.17187 | 0.272 | 0.074 | 6.721 | 45.166 |
| 123 | u4 | Validation | 17.25 | 21.56016 | 4.310 | 18.577 | 11.109 | 123.406 |

TABLE 1-continued

| Scan ID | Sample location ID | Name | Oil wt % Actual (retort) | Oil Wt % Calculated (calibration model) | Deviation | Square of Deviation | Deviation from Mean (0-41.0% set) | Square of Deviation |
|---|---|---|---|---|---|---|---|---|
| 124 | u4 | Validation | 17.25 | 21.00298 | 3.753 | 14.085 | 10.552 | 111.337 |
| 125 | u4 | Validation | 17.25 | 20.37414 | 3.124 | 9.760 | 9.923 | 98.462 |
| 126 | u4 | Validation | 17.25 | 20.85861 | 3.609 | 13.022 | 10.407 | 108.312 |
| 127 | u4 | Calibration | 17.25 | 19.00567 | 1.756 | 3.082 | 8.554 | 73.177 |
| 109 | u1 | Calibration | 21.93 | 22.26008 | 0.330 | 0.109 | 11.809 | 139.447 |
| 110 | u1 | Calibration | 21.93 | 24.84937 | 2.919 | 8.523 | 14.398 | 207.304 |
| 111 | u1 | Calibration | 21.93 | 23.63758 | 1.708 | 2.916 | 13.186 | 173.877 |
| 112 | u1 | Calibration | 21.93 | 22.53459 | 0.605 | 0.366 | 12.083 | 146.005 |
| 113 | u1 | Calibration | 21.93 | 22.3997 | 0.410 | 0.168 | 11.889 | 141.340 |
| 116 | u2 | Calibration | 24.39 | 23.13341 | −1.257 | 1.579 | 12.682 | 160.835 |
| 117 | u2 | Calibration | 24.39 | 23.2677 | −1.122 | 1.260 | 12.816 | 164.259 |
| 118 | u2 | Calibration | 24.39 | 23.72567 | −0.664 | 0.441 | 13.274 | 176.208 |
| 119 | u2 | Calibration | 24.39 | 24.59466 | 0.205 | 0.042 | 14.143 | 200.034 |
| 120 | u2 | Calibration | 24.39 | 22.89719 | −1.493 | 2.228 | 12.446 | 154.900 |
| 31 | m4 | Validation | 24.67 | 24.91048 | 0.240 | 0.058 | 14.459 | 209.067 |
| 32 | m4 | Validation | 24.67 | 23.81184 | −0.858 | 0.736 | 13.361 | 178.503 |
| 33 | m4 | Validation | 24.67 | 24.76685 | 0.097 | 0.009 | 14.316 | 204.934 |
| 34 | m4 | Validation | 24.67 | 22.96009 | −1.710 | 2.924 | 12.509 | 156.469 |
| 137 | u11 | Calibration | 28.19 | 25.46085 | −2.729 | 7.448 | 15.010 | 225.286 |
| 138 | u11 | Calibration | 28.19 | 24.99759 | −3.192 | 10.191 | 14.546 | 211.594. |
| 139 | u11 | Calibration | 28.19 | 24.44078 | −3.749 | 14.057 | 13.989 | 195.705 |
| 140 | u11 | Calibration | 28.19 | 25.62389 | −2.566 | 6.585 | 15.173 | 230.207 |
| 141 | u11 | Calibration | 28.19 | 24.76237 | −3.428 | 11.749 | 14.311 | 204.806 |

TABLE 2

Calibration Data Point Statistical Summary of Table 1

| Range (% Hydrocarbons) | Number of Data Points | Mean | Standard Deviation |
|---|---|---|---|
| 0-4.0% | 20 | 1.910 | 0.930 |
| 4.1-8.0% | 35 | 6.127 | 1.032 |
| 8.1-41.0% | 43 | 17.944 | 1.855 |
| 0-41.0% | 98 | 10.451 | 1.438 |

Figure 3:
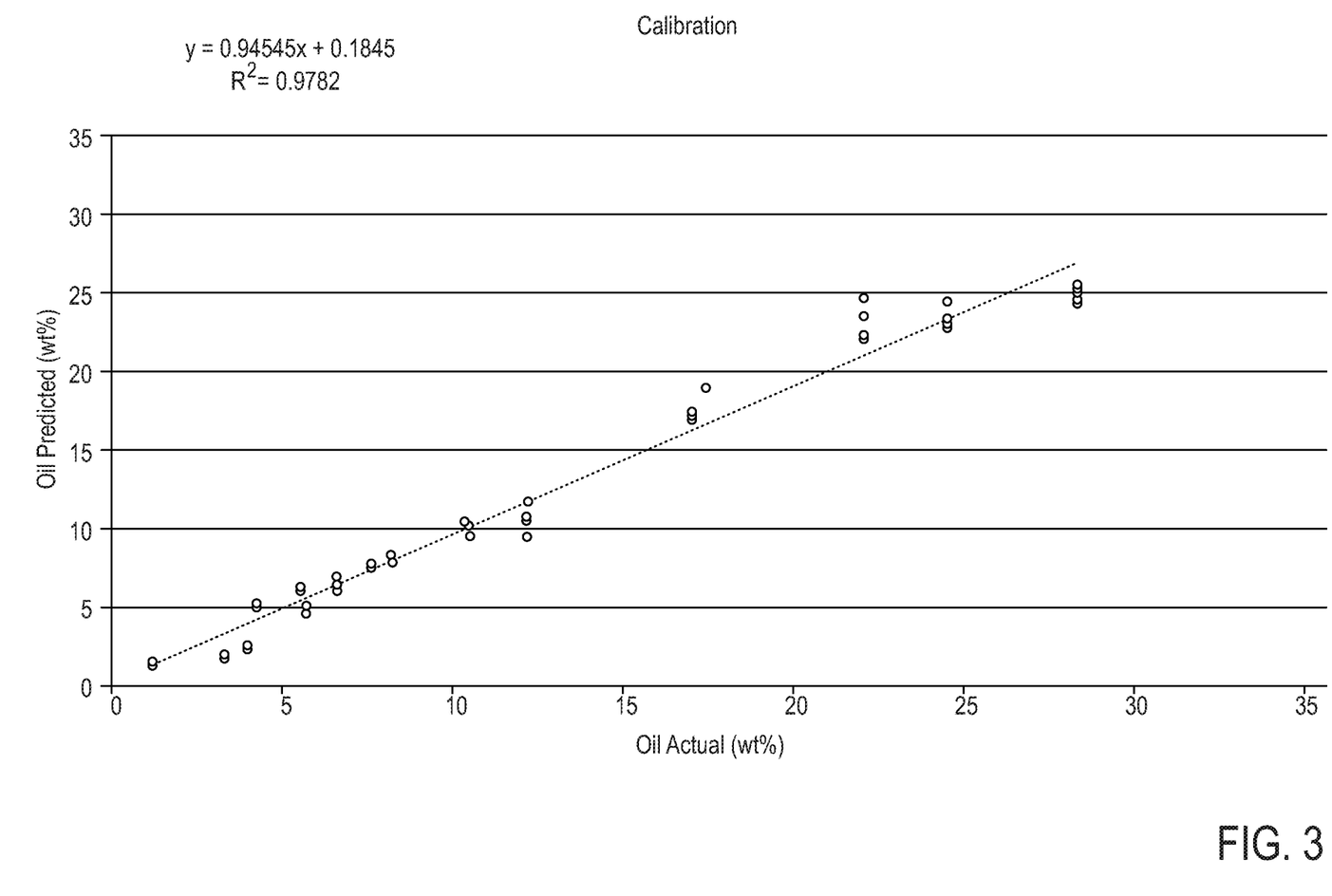
FIG. 3 is a graph illustrating an NIR chemometric model of calculated hydrocarbon concentration vs. actual hydrocarbon concentration determined by retort for drilled solids samples.

FIG. 3 shows a PLS calibration model correlates the predicted concentration of hydrocarbons of the drilled solids samples to the actual concentration from the retort. As shown in FIG. 3, the resulting NIR calibration model has a correlation coefficient $R^2$ of 0.9782, a promising finding. The handheld NIR device 10, then, is a good tool for quantifying the hydrocarbon content in drilling cuttings. Additionally, the method is very time efficient, requiring only three seconds to generate the hydrocarbon concentration level. Relative to the retort method, the disclosed method is 2400 times faster. This work demonstrates the successful use of handheld NIR spectroscopy in the compositional analysis of drilling fluid, achieving time, accuracy and cost improvements over existing methods.

Figure 4:
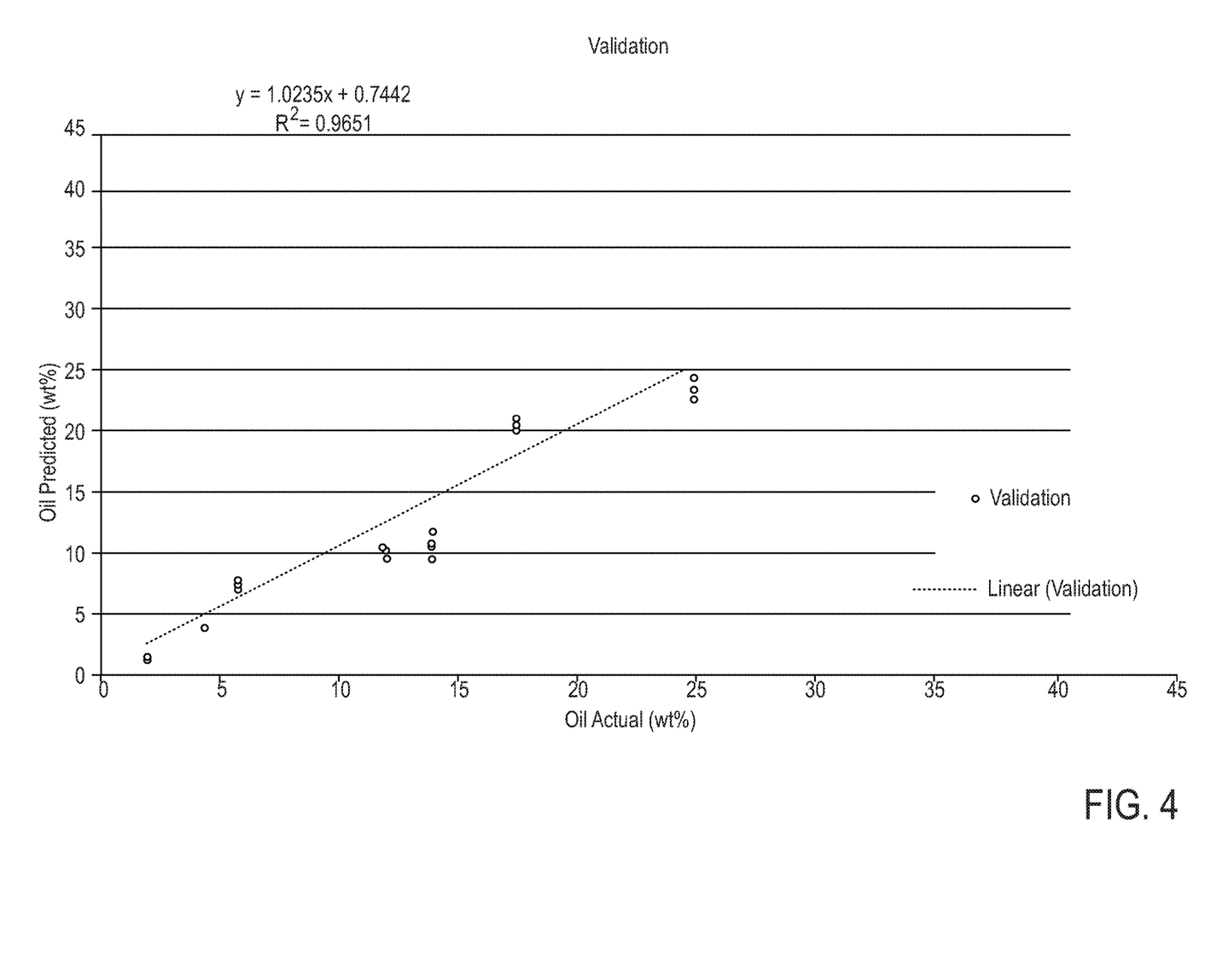
FIG. 4 is a graph illustrating a validation of calculated hydrocarbon concentration vs. actual hydrocarbon concentration determined by retort for validation drilled solids samples.

The predictions of the mean spectra of 10 samples with this calibration model are represented in FIG. 4, demonstrating good agreement with the reference retort values over the 1-25 wt % concentration range.

For the purposes of this specification and appended claims, unless otherwise indicated, all numbers expressing quantities, percentages or proportions, and other numerical values used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent.

Unless otherwise specified, the recitation of a genus of elements, materials or other components, from which an individual component or mixture of components can be selected, is intended to include all possible sub-generic combinations of the listed components and mixtures thereof. Also, "comprise," "include" and its variants, are intended to be non-limiting, such that recitation of items in a list is not to the exclusion of other like items that may also be useful in the materials, compositions, methods and systems of this invention.

What is claimed is:

1. A method for determining a concentration of hydrocarbons in drilled solids removed from a well on location at a drilling rig site, comprising:
  a. collecting, homogenizing and dividing a plurality of drilled solids samples having been removed from a drilling fluid used to drill the well wherein the plurality of drilled solids samples is collected on location at the drilling rig site and divided into a first set of drilled solids samples and a second set of drilled solids samples wherein the plurality of drilled solids samples has a water content of from 0.1 to 10 wt;
  b. analyzing the first set of drilled solids samples using a retort in a laboratory to obtain hydrocarbon concentration data;
  c. without drying or adding solvent to the second set of drilled solids samples, placing each of the second set of drilled solids samples into a clear container such that at least a portion of the clear container makes visible the drilled solids within the clear container from an exterior of the clear container;
  d. analyzing the second set of drilled solids samples using a handheld near infrared spectrometer having a diffuse reflectance window to obtain near infrared diffuse reflectance data wherein each of the clear containers is contacted with the diffuse reflectance window such that the IR source from the handheld device can pass to the drilled solids sample within the clear container without opening the clear container, wherein a plurality of replicate spectra of near infrared diffuse reflectance data are obtained for separate drilled solids samples and the near infrared diffuse reflectance data obtained are an average of the replicate spectra;

e. applying partial least squares regression analysis to correlate the hydrocarbon concentration data obtained using the retort with the near infrared diffuse reflectance data to generate a site specific predictive model for hydrocarbon concentration for the drilling rig site including integrating peak area of the near infrared diffuse reflectance data in the combination and first overtone spectral bands for CH, $CH_2$ and $CH_3$ to indicate hydrocarbon concentration based on the partial least squares regression analysis to correlate the hydrocarbon concentration data with the near infrared diffuse reflectance data;

f. analyzing a plurality of validation drilled solids samples taken from the rig site having unknown hydrocarbon concentration using the handheld near infrared spectrometer to obtain near infrared diffuse reflectance data for the validation drilled solids samples wherein the validation drilled solids samples have a water content of from 0.1 wt % to 10 wt % and each of the validation drilled solids samples is pressed against the diffuse reflectance window with sufficient pressure to ensure intimate contact between the sample and the diffuse reflectance window;

g. using the near infrared diffuse reflectance data for the validation drilled solids samples to predict the hydrocarbon concentration of the validation drilled solids samples using the site specific predictive model;

h. measuring the hydrocarbon concentration of the validation drilled solids samples using a retort; and i. comparing the predicted hydrocarbon concentration of the validation drilled solids samples with the hydrocarbon concentration of the validation drilled solids samples as measured using a retort to validate the predictive model.

2. The method of claim 1 further comprising analyzing a drilled solids sample taken at the rig site having an unknown hydrocarbon concentration using the handheld near infrared spectrometer to obtain near infrared diffuse reflectance data for the drilled solids sample; and using the site specific predictive model to estimate the hydrocarbon concentration of the drilled solids sample.

3. The method of claim 2 wherein the drilled solids sample is taken downstream of solids control equipment at the rig site.

4. The method of claim 1 further comprising continuously gathering NIR diffuse reflectance data from a NIR sensor located in a section of pipe at the rig site having drilled solids having unknown hydrocarbon concentration passing therethrough; and using the site specific predictive model to continuously monitor the hydrocarbon concentration of the drilled solids passing through the section of pipe.

5. The method of claim 4 wherein the section of pipe is located downstream of solids control equipment at the rig site.

6. The method of claim 1 wherein the handheld near infrared spectrometer obtains near infrared diffuse reflectance data within 3 seconds.

7. The method of claim 1 wherein the combination and first overtone spectral bands for CH, $CH_2$ and $CH_3$ is over a wave number of from $4300$ $cm^{-1}$ to $8000$ $cm^{-1}$.

8. The method of claim 1 wherein the drilled solids comprise hydrocarbons selected from the group consisting of lubricant oil, base oil, grease, diesel and combinations thereof.

9. The method of claim 1 wherein the container is selected from the group consisting of a clear plastic bag, a clear plastic bottle and a clear glass bottle.

10. The method of claim 1 wherein the plurality of drilled solids samples has a water content of from 1 to 5 wt % and the validation drilled solids samples have a water content of from 1 to 5 wt %.

11. The method of claim 1, wherein the applying partial least squares regression analysis further comprises using three factor correlation to correlate the hydrocarbon concentration data obtained using the retort with the near infrared diffuse reflectance data to generate the site specific predictive model.

12. The method of claim 2 or claim 4 further comprising disposing of the drilled solids if the estimated hydrocarbon concentration is below a predetermined maximum concentration.

13. The method of claim 2 or claim 4 further comprising segregating the drilled solids if the estimated hydrocarbon concentration is above a predetermined maximum concentration.

* * * * *